United States Patent
Shaikho

[11] Patent Number: 5,968,458
[45] Date of Patent: Oct. 19, 1999

[54] STERILIZING APPARATUS

[76] Inventor: Ahmed Adnan Shaikho, H 209, Rd. 3502, C.935, E. Rifala, Bahrain

[21] Appl. No.: 08/801,943

[22] Filed: Feb. 14, 1997

[30] Foreign Application Priority Data

Feb. 16, 1996 [GB] United Kingdom ............... 9603255

[51] Int. Cl.$^6$ ...................................... A61L 2/18
[52] U.S. Cl. ................ 422/300; 422/292; 15/104.92; 206/370; 134/170; 134/158
[58] Field of Search ................... 422/292, 300, 422/301; 206/370; 15/104.92; 134/170, 158

[56] References Cited

U.S. PATENT DOCUMENTS 4,421,059  12/1983  Cousino ........................ 119/51.12
4,676,839  6/1987  Osborn .......................... 15/104.92
5,222,271  6/1993  Eganhouse .................... 15/104.92

*Primary Examiner*—Leigh McKane
*Assistant Examiner*—Fariborz Moazzam
*Attorney, Agent, or Firm*—Hodgson, Russ, Andrews, Woods & Goodyear LLP

[57] ABSTRACT

Apparatus for sterilizing specula is described. The apparatus comprises a bath suitable for containing disinfectant solution; a plurality speculum supporting means located within the bath; a rotatable plate located above the speculum supporting means, the rotatable plate having an aperture disposed in such a manner that on rotation of the plate, the aperture may be moved from a position above a first speculum supporting means to a position above a second speculum supporting means; and means for rotating the rotatable plate in one direction only.

14 Claims, 1 Drawing Sheet

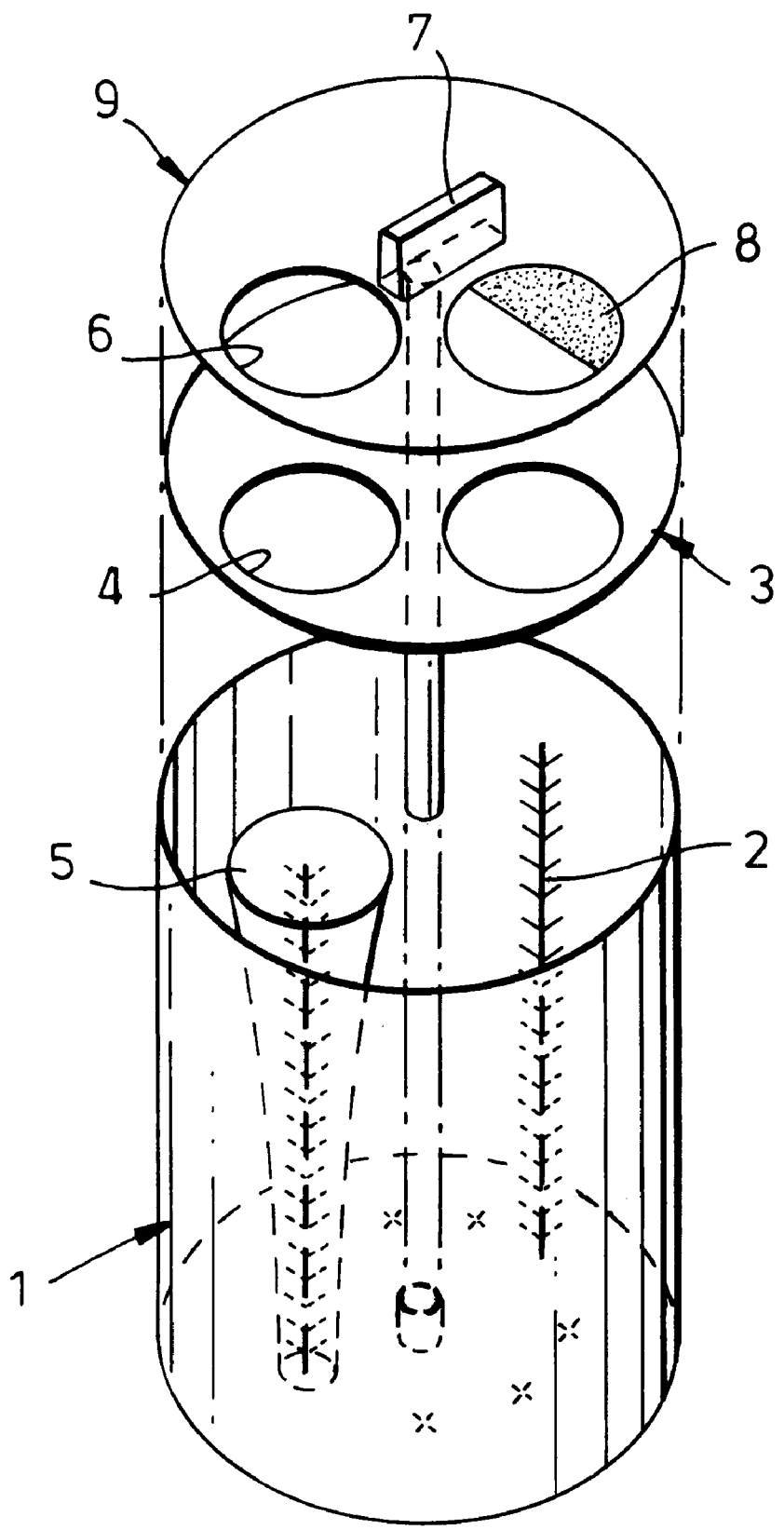

STERILIZING APPARATUS

The present invention relates to apparatus for sterilizing ear specula.

Wherever examination of a patient is to occur it is important that the medical equipment used to examine the patient is sterile to prevent the spread of infection between patients. For this reason many small items of equipment, for example needles, are now single use. That is to say they are supplied to the medical practitioner in a sealed sterile package and after use the item is disposed of.

Whilst this arrangement is acceptable for small, low cost items, it is not economical for larger, more expensive items such as ear specula. Equipment of this type is commonly sterilised prior to use by being immersed in a bath of a disinfectant solution. The specula are laid in the bath and are removed at random from the bath by the medical practitioner prior to use. After a speculum has been used it is returned to the bath.

This arrangement has certain disadvantages and drawbacks. Firstly, it is difficult for the medical practitioner to assess whether a particular speculum has been immersed in the disinfectant solution for sufficient time to ensure that it has been sterilised. This problem is particularly acute if the specula are all identical in appearance. In this case, it is difficult for the medical practitioner to ensure that the speculum that is removed from the bath to treat a patient is that which has been in the bath for the longest period.

Further, in use specula become blocked with ear wax. In view of the nature of the wax it is not readily removed from the specula during immersion in the disinfectant solution.

We have now discovered that the aforementioned problems may be addressed by the provision of a sterilization bath in which the specula are located in a particular arrangement within the bath and the bath is provided with means to prevent the practitioner using the item most recently introduced into the bath.

Thus, according to the present invention there is provided apparatus for sterilizing specula comprising: a bath suitable for containing disinfectant solution; a plurality of speculum supporting means located within the bath; a rotatable plate located above the speculum supporting means, the rotatable plate having an aperture disposed in such a manner that on rotation of the plate, the aperture may be moved from a position above a first speculum supporting means to a position above a second speculum supporting means; and means for rotating the rotatable plate in one direction only.

Thus in use the medical practitioner replaces a used speculum into the bath via the aperture in the rotatable disc such that it is support by the speculum supporting means. He then causes the rotatable disc to rotate such that the aperture is located above a second speculum which may be then extracted for use with the next patient.

The number of speculum supporting means provided are preferably selected such that the total time required to use each of the speculum housed in sequence within the apparatus is equal to, or greater than, the time required to ensure that sterilization is complete.

The rotatable plate preferably forms the closure to the bath. Where the rotatable plate does not close the upper opening of the bath, a separate closure means may be provided.

The speculum supporting means are preferably projections extending from the base of the container. Each projection is preferably configured such that it removes any deposits, such as ear wax, from the surface of the speculum as it is inserted over the projection or removed therefrom.

The projections are preferably brushes. The apparatus preferably additionally includes a plate located above the base of the container having a plurality of apertures located therein, said apertures, which correspond in location to the speculum supporting means, provide additional support for the speculum. This is particularly useful if the speculum supporting means are brushes which have insufficient inherent strength to support the specula. The plate is preferably fixed to the walls of the bath in a position such that the lower two thirds of the speculum pass through the aperture.

The rotation of the rotatable plate is preferably restricted to movement in one direction by a ratchet means; although any suitable means may be utilised.

The rotatable plate may additionally include a timer which indicates when the disinfectant is no longer effective due to the passage of time or the number of specula that have been treated within the apparatus.

The timer preferably comprises a marked disc which is rotatable about its central axis and which is caused to rotate by friction with the wall of the bath. The disc may be located beneath the rotatable plate which may include an aperture such that at least a portion of the disc is visible from above the rotatable plate. The marking on the disc may comprise colouring each semicircular segment of the disc a different colour. In this arrangement, the aperture in the rotatable disc will correspond in size to the coloured half disc. When the colour of the portion of the disc visible from above the plate has completely changed, the disinfectant will require refreshing. The size of the disc will be chosen to correspond to the number of speculum to be treated in the apparatus and the concentration of the disinfectant solution used.

The apparatus may additionally include means for draining the disinfectant solution from the bath. The means may be an aperture located in the base of the bath or in the lower portion of one of the walls of the bath. In use, the aperture will be plugged to prevent leakage of the disinfectant solution from the bath. The aperture may be plugged by any suitable means. However, a bung or a screw is particularly preferred. When the disinfectant solution is no longer effective, the aperture may be unplugged and the solution allowed to drain out. In order to facilitate drainage of the solution, the apparatus may be provided with a stand or may have legs to raise it from the surface on which it stands. The apparatus may additionally include a tray or similar means to collect the disinfectant solution as it is released from the bath. The tray is preferably removed from the apparatus for ease of disposal of the solution.

The present invention will now be described, by way of example, with reference to the accompanying drawing in which:

FIG. 1 is an exploded view of a preferred embodiment of the present invention.

The sterilizing apparatus of the present invention preferably comprises a bath 1 having a plurality of brushes 2 extending from its base. For clarity, FIG. I illustrates only two brushes. Further brushes are located at sites X. In a particularly preferred arrangement there are six brushes.

A plate 3 is located within the bath. The plate has apertures 4 which are located such that each brush 2 passes through an aperture 4. The plate is located such that when a speculum 5 is passed onto the brush through the aperture the upper third of the speculum remains above the disc.

The rotatable plate 9 of the apparatus provides the lid for the bath One aperture 6 is situated in the plate such that on assembly it corresponds to the location of one of the combinations of a brush 2 and an aperture in the plate 3. A handle 7 enables the medical practitioner to rotate the rotatable plate in one direction only. Thus, in use the medical practitioner having used one speculum inserts it through aperture 6, a corresponding aperture 4 and locates it on a brush 2. The handle 7 is then turned such that the aperture 6 moves such that access to the speculum just inserted is denied and access to a second speculum (not shown) is achieved.

A timer 8 consisting of a disc, half of which is coloured, is provided in association with the rotatable plate 9 such that on rotation of the rotatable plate the disc rotates due to friction with the wall of the bath. The disc is preferably divided in half, each half being differently coloured. A second aperture in the shape of a semicircular segment is provided in the rotatable plate above the disc such that only half of the disc is visible. As the rotatable plate is rotated in use the colour of the segment of the disc visible will change. When the segment visible has completely changed colour, the medical practitioner will be alerted to the fact that the disinfectant solution is no longer effective and that it should be refreshed.

It will be understood that whilst the present invention has been described with reference to ear specula, minor modifications may be made to adapt the device such that it can be used to sterilize other medical equipment.

I claim:

1. Apparatus for sterilizing specula comprising:
 a bath containing disinfectant solution; a plurality of speculum supporting means located within the bath; each of said speculum supporting means being shaped and disposed so as to fit within an end of a speculum; a rotatable plate located above the speculum supporting means; the rotatable plate having an aperture disposed in such a manner that on rotation of the plate, the aperture may be moved from a position above a first speculum supporting means to a position above a second speculum supporting means; and means for rotating the rotatable plate in one direction only.

2. Apparatus according to claim 1 wherein the rotatable plate forms a closure to the bath.

3. Apparatus according to claim 1 wherein the speculum supporting means are projections extending from a base of a container.

4. Apparatus according to claim 3 wherein each projection is configured such that it removes ear wax from a surface of the speculum as it is inserted over the projection or removed therefrom.

5. Apparatus according to claim 3 wherein the projections are brushes.

6. Apparatus according to claim 1 wherein the apparatus additionally includes a supporting plate located above the base of the container having a plurality of supporting apertures located therein, said supporting apertures corresponding to the speculum supporting means to provide additional support for the speculum.

7. Apparatus according to claim 6 wherein the supporting plate is fixed to the walls of the bath in a position such that in use a lower two thirds of the speculum pass through the supporting aperture.

8. Apparatus according to claim 1 wherein the rotation of the rotatable plate is restricted to movement in one direction by a ratchet means.

9. Apparatus according to claim 1 wherein the rotatable plate additionally includes a timer which indicates when the disinfectant solution is no longer effective due to a passage of time or the number of specula that have been treated within the apparatus.

10. Apparatus according to claim 9 wherein the timer comprises a marked disc which is rotatable about its central axis and which is caused to rotate by friction with the wall of the bath.

11. Apparatus according to claim 10 wherein the disc is located beneath the rotatable plate which includes an aperture such that at least a portion of the disc is visible from above the rotatable plate.

12. Apparatus according to claim 10 wherein the marking on the disc comprises colouring one half of the disc.

13. Apparatus for sterilizing specula comprising; a bath containing disinfectant solution; a plurality of brushes located within the bath for cleaning and supporting specula; a rotatable plate located above the speculum supporting brushes; the rotatable plate having an aperture dispersed in such a manner that on rotation of the plate, the aperture may be moved from a position above a first brush to a position above a second brush; a means for rotating the rotatable plate in one direction only; and a plate located above a base of the container having a plurality of apertures located therein, said apertures corresponding to the brushes to provide additional support for the speculum.

14. Apparatus according to claim 13 additionally including a timer which indicates when the disinfectant solution is no longer effective due to a passage of time or the number of specula that have been treated within the apparatus.

\* \* \* \* \*

UNITED STATES PATENT AND TRADEMARK OFFICE
CERTIFICATE OF CORRECTION

PATENT NO. : 5,968,458
DATED : October 19, 1999
INVENTOR(S) : Ahmed Adnan Shaikho It is certified that error appears in the above-identified patent and that said Letters Patent is hereby corrected as shown below:

Column 4,
Line 35, "dispersed" should be -- disposed --.

Signed and Sealed this

Thirtieth Day of July, 2002

Attest:

Attesting Officer

JAMES E. ROGAN
Director of the United States Patent and Trademark Office